United States Patent [19]
Doan et al.

[11] Patent Number: 5,755,767
[45] Date of Patent: May 26, 1998

[54] ANTI-DISLODGMENT AND ANTI-PERFORATION DISTAL TIP DESIGN FOR TRANSVENOUS LEAD

[75] Inventors: Phong D. Doan, Stevenson Ranch; Benedict Gomperz, North Hollywood; Shahram Moaddeb, Woodland Hills, all of Calif.

[73] Assignee: Pacesetter, Inc., Sylmar, Calif.

[21] Appl. No.: 692,023

[22] Filed: Aug. 2, 1996

[51] Int. Cl.⁶ .................................................. A61N 1/05
[52] U.S. Cl. .................................... 607/126; 607/127
[58] Field of Search ..................... 607/122, 126–128

[56] References Cited

U.S. PATENT DOCUMENTS

| | | | |
|---|---|---|---|
| 3,902,501 | 9/1975 | Citron et al. | 128/418 |
| 3,939,843 | 2/1976 | Smyth | 128/404 |
| 4,407,303 | 10/1983 | Akerstrom | 607/126 |
| 4,475,560 | 10/1984 | Tarjan et al. | 607/128 |
| 4,550,737 | 11/1985 | Osypka | 607/127 |
| 4,716,888 | 1/1988 | Wesner | 607/126 |
| 4,722,353 | 2/1988 | Sleutz | 607/128 |
| 4,796,643 | 1/1989 | Nakazawa | 607/128 |
| 5,522,876 | 6/1996 | Rusink | 607/127 |

FOREIGN PATENT DOCUMENTS

| | | | |
|---|---|---|---|
| 3300050 | 7/1984 | Germany | 607/126 |
| 733694 | 5/1980 | U.S.S.R. | 607/126 |

Primary Examiner—Lee S. Cohen

[57] ABSTRACT

A transvenous endocardial lead comprises an elongated flexible body member encompassing an electrical conductor which has an electrode at its distal end. A stabilizer adjacent the distal electrode extends outwardly from the flexible body member by a distance no greater than approximately one-half of the shortest distance between a longitudinal axis and the outer peripheral surface for minimizing dislodgment of the distal end from an intended implanted position into the myocardial tissue of the heart and for preventing penetration of the distal end of the flexible body member into the myocardial tissue. The stabilizer may be employed in conjunction with conventional active or passive fixation members and may take a variety of forms.

7 Claims, 4 Drawing Sheets

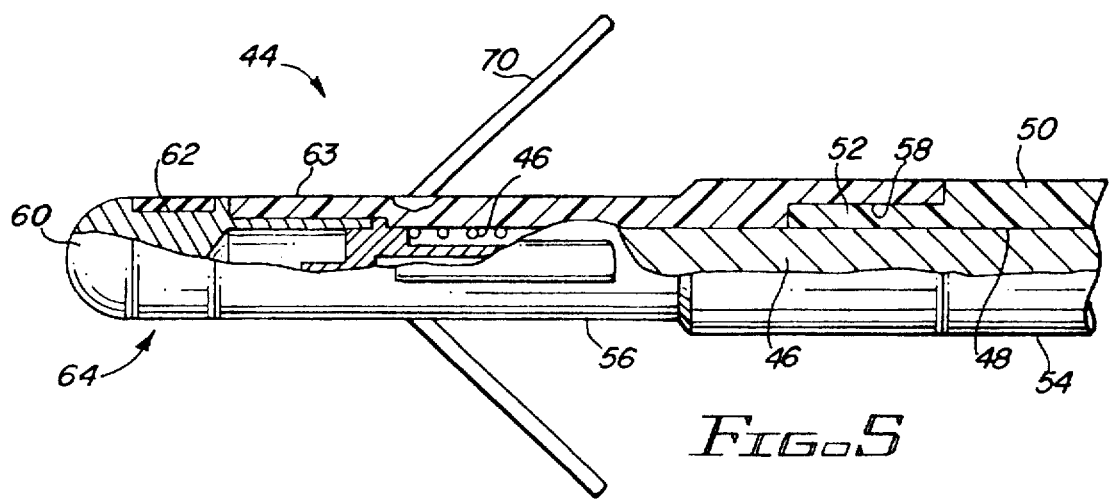
FIG. 5
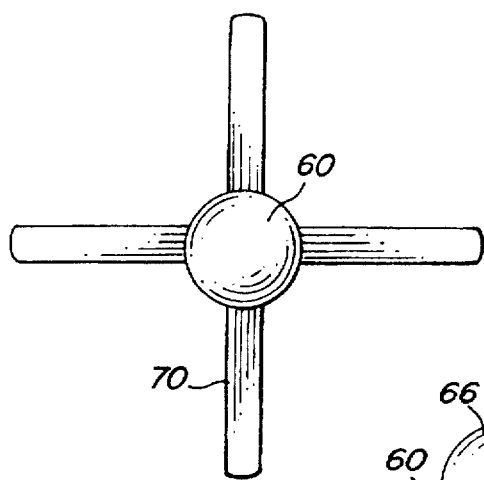
FIG. 5A
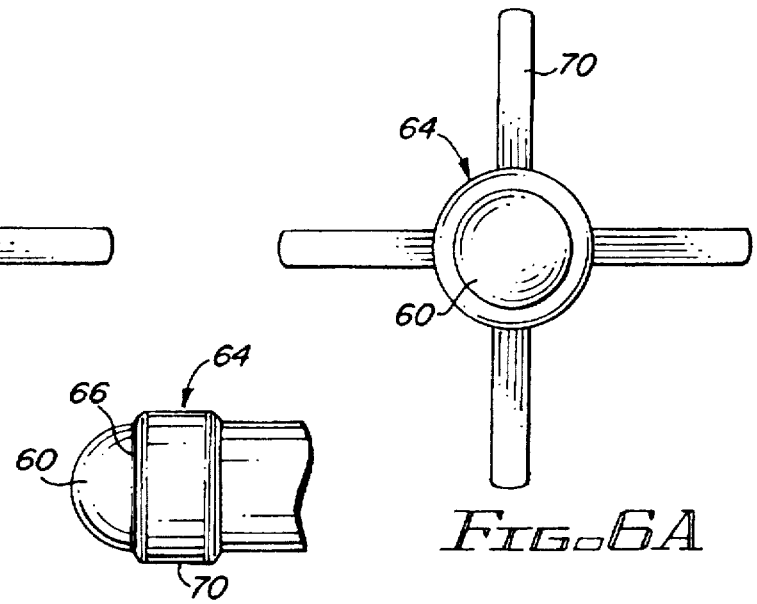
FIG. 6
FIG. 6A
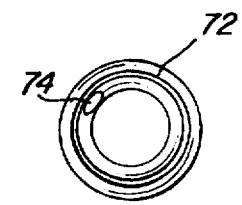
FIG. 7A
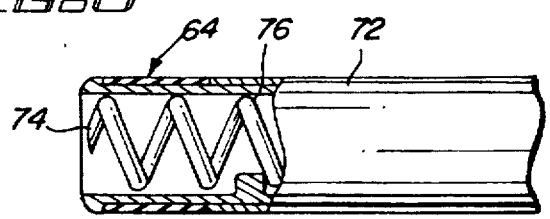
FIG. 7
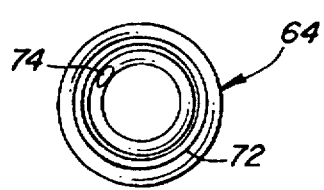
FIG. 8A
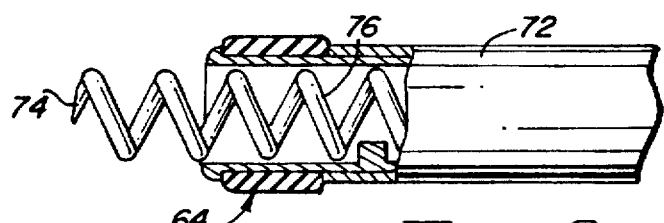
FIG. 8

1

ANTI-DISLODGMENT AND ANTI-PERFORATION DISTAL TIP DESIGN FOR TRANSVENOUS LEAD

FIELD OF THE INVENTION

This invention relates generally to transvenous leads carrying an endocardial electrode for electrical stimulation of the heart and, more particularly, to such a lead constructed to minimize dislodgment of the distal end of the transvenous lead from an intended implanted position and to prevent penetration of the distal end of the transvenous lead into and through the myocardial tissue of the heart.

BACKGROUND OF THE INVENTION

Electrical stimulation of heart action is well known and has been employed to counter a variety of heart dysfunctions. Dependent upon the particular dysfunction, optimal placement of the electrical contact point or points may vary. However, optimal electrode placement has often been sacrificed to other considerations such as minimization of the surgical risk and reliability of the electrode securement. To date, the greatest number of electrodes have been ventricular electrodes with the transvenous endocardial approach coming into the fore in recent years.

The advantage of a reliable electrical contact with the atrium are well-known. Such a contact would allow atrial pacing or atrial synchronized pacing thereby preserving the contribution of the atrial contraction on the overall cardiac output. Additionally, an atrial contact would be advantageously employed for arrhythmia management and other purposes which may not be accomplished through ventricular electrical stimulation. For reasons well known to those skilled in the art, the greatest advantages can be obtained through an electrical contact with the right atrium, the right atrial appendage often providing a suitable site.

The earliest transvenous pacing leads had large stimulating electrodes that had surface areas of approximately 100 mm$^2$. Such electrodes presented a very large surface area to the endocardium, which resulted in a very low pacing impedance, generally on the order of 250 ohms. Because current flow is inversely related to impedance, a large amount of current was drained from the power source with these leads. In addition, because the current was dispensed over a large surface area, resulting in a lower current density and a higher stimulation threshold. By the late 1970s, most pacing leads had cathodes with surface areas of approximately 8 to 12 mm$^2$ that produced impedance measurements of 400 to 600 ohms. At this time, further reductions in cathode size were thought to be potentially unsafe because of the effects of microdislodgment of tissue contact. Nevertheless, leads with 6-mm$^2$ or even 4-mm$^2$ electrodes were introduced and were found to be safe for long-term pacing and sensing. Today, serious consideration is being given to electrodes with surface areas of less than 2 mm$^2$ that provide acute and chronic impedance measurements of over 1,000 ohms.

Myocardium perforation caused by transvenous endocardial pacing/defibrillation leads historically has been a problem due to various causes but mainly from the stiffness and the small geometry of the lead distal end. Clinical complication as a result of this problem has been considered critical. Today, with the trend of the pacing industry to produce a small lead with a small steroid eluting tip electrode to enhance lead implantation handling and electrical performance, lead myocardium perforation could be a major problem if the distal tip design and lead body stiffness are not refined and improved.

Electrode dislodgment from its implantation site is probably the most common complication encountered when working with transvenous endocardial leads. Electrode instability is usually a complication of the implantation procedure and is not a lead-tissue problem (that is, an inflammatory reaction). Implantation includes lead performance issues such as stiffness and fixation devices. The great majority of lead dislodgment problems that alter the lead's electric performance are detected and corrected immediately by lead repositioning.

Migration of a dislodged lead out of the heart may be undetected for months in poorly managed patients with an intermittent dysrhythmia. Migration into the pulmonary artery, jugular vein, or an iliac vein can cause complications such as pulmonary embody and thrombosis of the vein. Once discovered, these leads should be removed and new leads implanted.

On occasion, leads break, and abandoned leads are sometimes cut and left unsecured. Although the incidence of migration is probably low, migration of severed or broken transvenous leads does occur and is potentially dangerous. Fatality secondary to lead migration of severed has been reported to be as high as 66%. For example, if the proximal lead tip is bouncing in the right ventricle causing a ventricular arrhythmia, it is life-threatening. Migrating severed leads have perforated the heart, causing hemorrhage or hemopericardium, and have formed vegetations, causing emboli to the lungs. These conditions mandate lead extraction. A severed lead coil in the right ventricle may cause acute symptoms and the scar tissue that forms lead-to-lead and lead-to-heart wall will compromise ventricular function over time. In asymptomatic patients, the potential exists for one of these complications to occur, making extraction a necessary condition. Hence, efforts to prevent dislodgment and migration of the distal end of a transvenous endocardial lead are of considerable importance.

Early examples of transvenous electrode devices on disclosed in U.S. Pat. No. 3,902,501 to Citron et al. and U.S. Pat. No. 3,939,843 to Smyth.

The Citron et al. patent provides an electrode uniquely adapted for use as an atrial electrode. The electrode may be positioned in the right atrial appendage. A plurality of pliant nonconductive tines are provided at the tip of the electrode to cooperate with the heart tissue, particularly the trabeculae found in the right atrial appendage, to maintain the electrode tip in electrical contact with the heart tissue while allowing a removal of the electrode should that prove necessary. Provision is also made for holding the tines against the electrode body during insertion while allowing their release when the tip is in position and after a test threshold measurement.

The Smyth patent provides a transvenous lead including a conductor encased in an insulating material which is generally inert in body fluids and tissues, the conductor terminating at an exposed electrically conductive electrode at, or adjacent to, the lead terminus. At least one tine extends from the casing adjacent the lead terminus for engaging the inner wall or trabeculae of an internal body organ or chamber to urge the electrode in a given, nominally transverse, direction. Through this transverse urging, the lead of the present invention may be employed in any body organ or chamber to urge the electrode against the organ or chamber side wall through the engagement of the tines with such trabeculae as might exist and/or the opposing sidewall of the organ or chamber. Also, the electrode may be positioned at any point along the lead that is within the influence of the tines.

SUMMARY OF THE INVENTION

It was in light of the prior art as just related that the present invention was conceived and has now been reduced to practice. According to the invention, a transvenous endocardial lead comprises an elongated flexible body member encompassing an electrical conductor which has an electrode at its distal end. A stabilizer adjacent the distal electrode extends outwardly from the flexible body member by a distance no greater than approximately one-half of the shortest distance between a longitudinal axis and the outer peripheral surface for minimizing dislodgment of the distal end from an intended implanted position and for preventing penetration of the distal end of the flexible body member into the myocardial tissue. The stabilizer may be employed in conjunction with conventional active or passive fixation members. The stabilizer may take a variety of forms. In one instance, the stabilizer may include a swellable collar extending around the perimeter of the flexible body member adjacent the distal electrode and having an outer surface which, in a diminished condition, is generally flush with the outer peripheral surface and is expandable to a swelled condition projecting away from the outer peripheral surface, the collar being composed of an inert material which in the dry state remains in a diminished condition but which when exposed to body fluid will absorb the fluid and expand to the swelled condition, and which is pliant yet with sufficient rigidity to engage and be entrapped within fibrous tissue of the heart and prevent further distal travel of the endocardial lead into the myocardial tissue. Alternatively, the stabilizer may include a continuous annular flange, or a plurality of flange members fixed on the flexible body member and projecting outwardly from the outer peripheral surface at spaced locations around its perimeter. In another instance, the stabilizer may include a plurality of outwardly extending nonconductive mini tines on the flexible body member at a plurality of spaced locations around the perimeter thereof and forming a generally acute angle with the outer peripheral surface. In yet another instance, the stabilizer may include a continuous annular ridge fixed on the flexible body member and projecting outwardly from its outer peripheral surface.

Accordingly, a primary object of the present invention is to provide a transvenous lead carrying an endocardial electrode for electrical stimulation of the heart and including a stabilizer to minimize dislodgment of the distal end of thereof from an intended implanted position and, at the same time, to prevent penetration of the distal end of the transvenous lead into and through the myocardial tissue of the heart.

Another object of the invention is to provide such a novel transvenous lead wherein the stabilizer includes a swellable collar fixed on and extending around the perimeter of said outer peripheral surface of a flexible body member adjacent a distal electrode, the collar having an outer surface which, in a diminished condition, is generally flush with the outer peripheral surface and is expandable to a swelled condition projecting away from the outer peripheral surface, the collar being composed of a material which is generally inert to body fluids and tissue, which in the dry state remains in a diminished condition but which when exposed to body fluid will absorb the fluid and expand to the swelled condition, and which is pliant yet with sufficient rigidity to engage and be entrapped within fibrous tissue of the heart and prevent further distal travel of the endocardial lead into the myocardial tissue of the heart distally beyond the stabilizer.

A further object of the invention is to provide such a novel transvenous lead wherein the flexible body member has a continuous groove in and encircling the peripheral surface and lying in a plane generally perpendicular to said longitudinal axis and wherein the swellable collar is embedded in the continuous groove and extends around the perimeter of the flexible body member adjacent the distal electrode.

Yet another object of the invention is to provide such a stabilizer used in combination with either active (screw-in) or passive (tined, finned) fixation leads intended to minimize the myocardium perforation without compromising the small introduction-size lead body and small tip electrode features.

Still a further object of the invention is to provide such a novel transvenous lead wherein the stabilizer includes a continuous annular flange fixed on the flexible body member and projecting outwardly from the outer peripheral surface thereof, the annular flange being composed of a material which is generally inert to body fluids and tissue and which is pliant yet with sufficient rigidity to engage and be entrapped within fibrous tissue of the heart.

Yet a further object of the invention is to provide such a novel transvenous lead wherein the stabilizer includes a plurality of flange members fixed on the flexible body member and projecting outwardly from the outer peripheral surface thereof at spaced locations around the perimeter thereof, the flange members being composed of a material which is generally inert to body fluids and tissue and which is pliant yet with sufficient rigidity to engage and be entrapped within fibrous tissue of the heart.

Still a further object of the invention is to provide such a novel transvenous lead wherein the stabilizer includes a plurality of nonconductive mini-tine means on the flexible body member and extending from the outer peripheral surface at a plurality of spaced locations around the perimeter thereof for cooperating with the myocardial tissue of the heart to hold the flexible body member in position, the mini-tine means forming a generally acute angle with the outer peripheral surface and being entirely of a material which is pliant yet with sufficient rigidity to engage and be entrapped within fibrous tissue of the heart.

Still another object of the invention is to provide such a novel transvenous lead wherein the stabilizer includes a continuous annular ridge fixed on the flexible body member and projecting outwardly from the outer peripheral surface thereof, the annular ridge being composed of a material which is generally inert to body fluids and tissue and which is pliant yet with sufficient rigidity to engage and be entrapped within fibrous tissue of the heart.

Yet another object of the invention is to provide such a novel transvenous lead wherein the nominal projected surface area the distal electrode is in the range of approximately 0.5 to 3.0 $mm^2$.

Other and further features and advantages of the present invention will become more apparent from the following detailed description, taken in conjunction with the accompanying drawings which illustrate, by way of example, the principles of the invention. Throughout the specification, like numerals refer to like parts.

BRIEF DESCRIPTION OF THE DRAWINGS

The accompanying drawings illustrate the invention:

FIG. 5 is a detail side elevation view, partially cut away and in section, illustrating one embodiment of the present invention in its diminished condition;

FIG. 5A is a front elevation view of the invention illustrated in FIG. 5;

FIGS. 6 and 6A are, respectively, a detail side elevation view, and a front elevation view, similar to FIGS. 5 and 5A, illustrating that embodiment of the present invention in its expanded condition;

FIGS. 7 and 7A are, respectively, a detail side elevation view, and a front elevation view, similar to FIGS. 5 and 5A, illustrating that embodiment of the invention in combination with active fixation means and in its diminished condition;

FIGS. 8 and 8A are, respectively, a detail side elevation view, and a front elevation view, similar to FIGS. 6 and 6A, illustrating that embodiment of the invention in combination with active fixation means and in its expanded condition;

DETAILED DESCRIPTION OF THE PREFERRED EMBODIMENT

Figure 1:
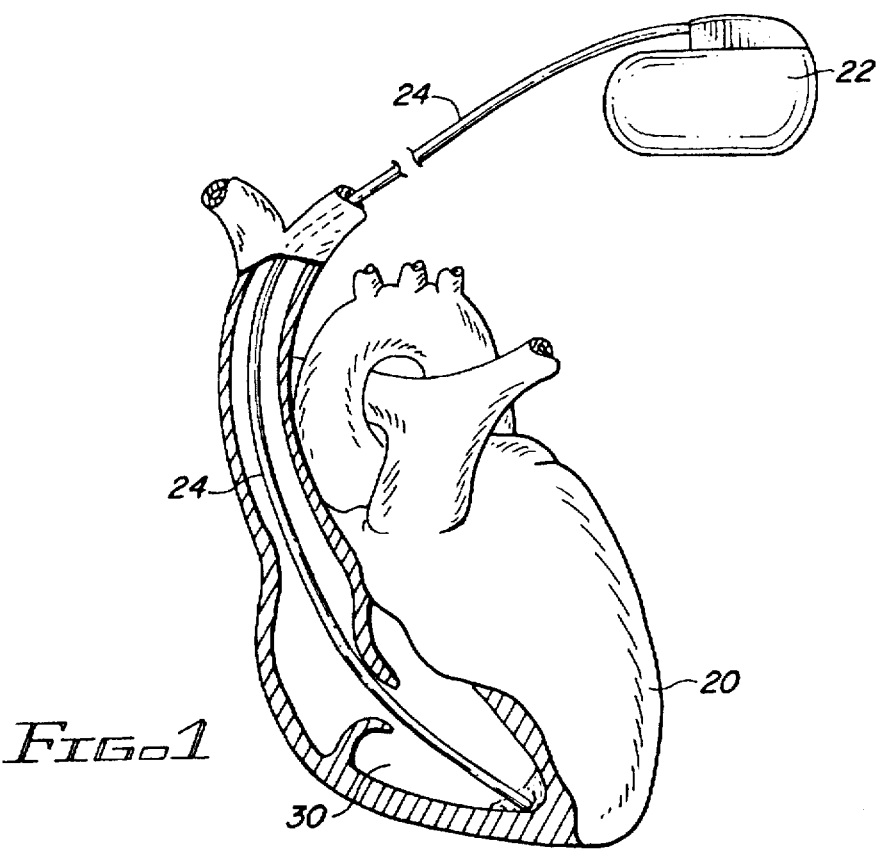
FIG. 1 is a diagrammatic elevation view, partly in section, of a heart pacing system embodying the present invention.

Turn now to the drawings and, initially, to FIGS. 1–4 which illustrate implantable medical devices and transvenous endocardial leads for attachment at their distal ends to the tissue of the heart 20 for its appropriate stimulation. In FIG. 1, a pacemaker 22 is illustrated as being implanted in the upper chest region of a user with a transvenous endocardial lead 24 extending through the right atrium 26 (FIG. 3) and the tricuspid valve 28 into the right ventricle 30. An electrically conductive electrode 32, or pacing tip, at the distal end of a head member 34 integral with the lead 24 is positioned in engagement with the myocardial tissue of the heart 20.

Figure 2:
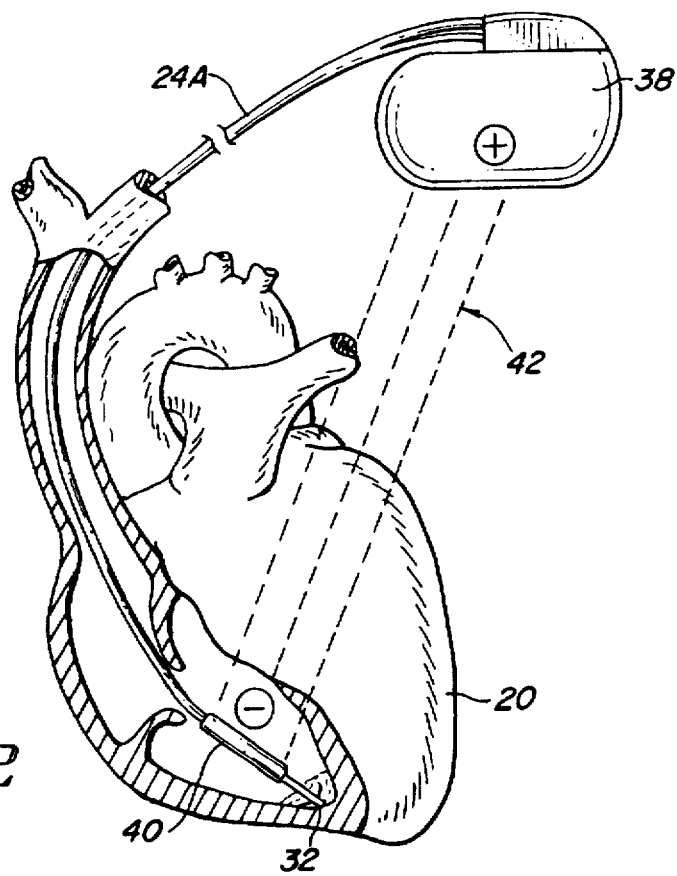
FIG. 2 is a diagrammatic elevation view, partly in section, of a heart defibrillation system embodying the present invention.
Figure 3:
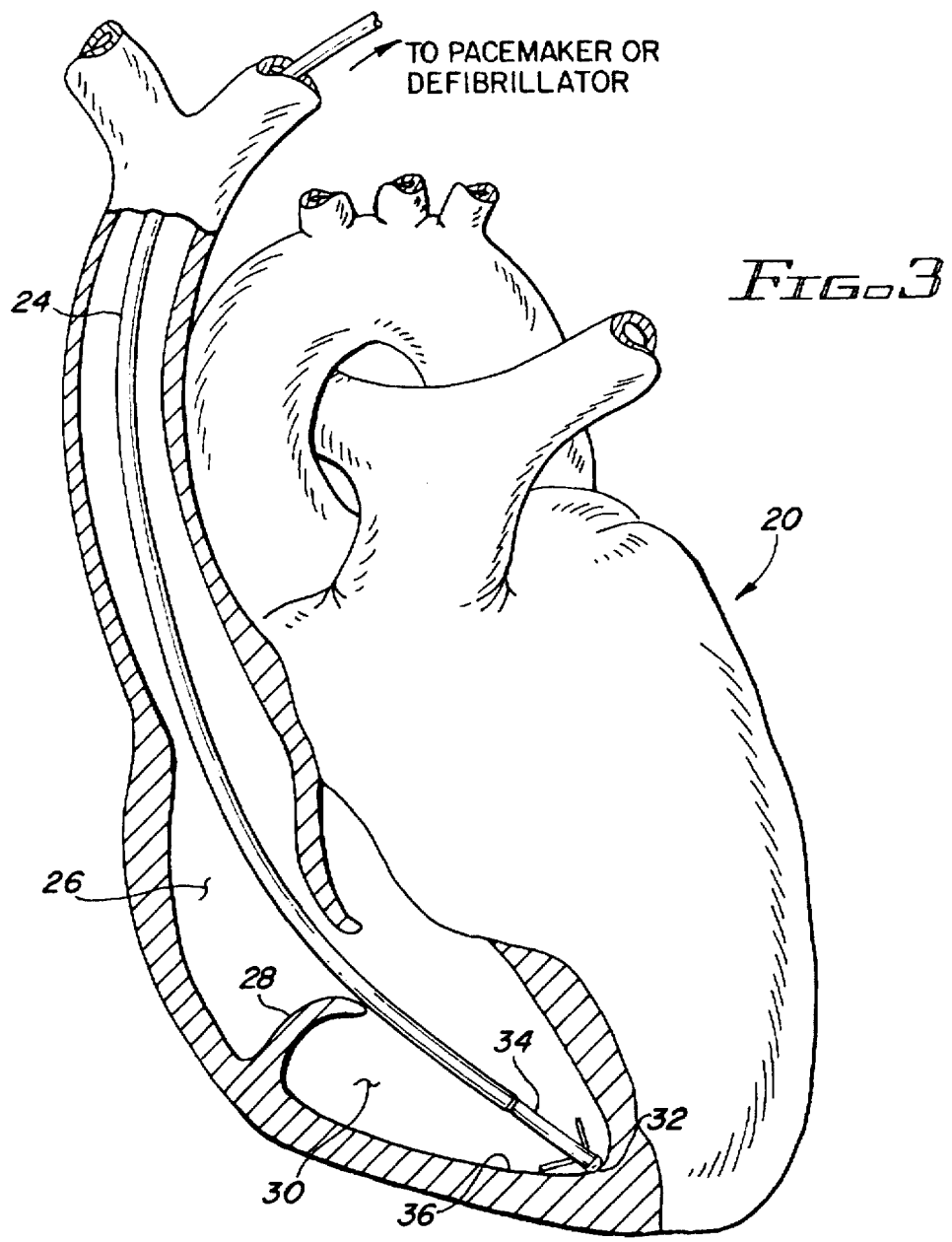
FIG. 3 is an enlarged detail side elevation view, in section, of structure illustrated in FIG. 1.
Figure 4:
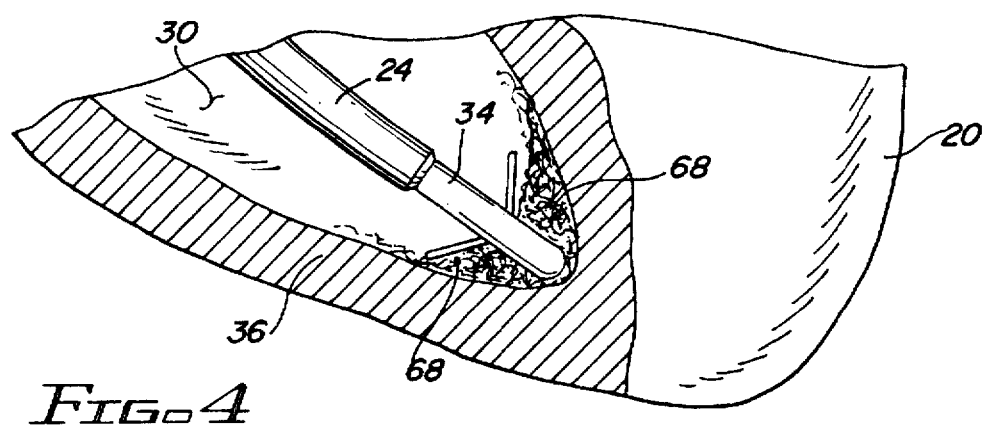
FIG. 4 is a further enlarged detail side elevation view, in section, of structure illustrated in FIG. 3.

In similar fashion, in FIG. 2, a defibrillator 38 is illustrated as being implanted in the upper chest region of a user with a transvenous endocardial lead 24A, as in the instance of the lead 24 extending through the right atrium 26 and the tricuspid valve 28 into the right ventricle 30. In this instance, a defibrillation electrode 40 located proximally of the pacing tip, or distal, electrode 32 completes the electrical circuit with the defibrillator 38 as diagrammatically indicated by the electrical current lines 42. The present invention is applicable to either pacing or defibrillation leads because the defibrillation lead 24A may also have a pacing tip electrode 32 for pacing back-up or for antitachyarrhythmia therapy. However, in the ensuing disclosure, for simplicity, discussion will be limited to the pacing configuration.

Turn now to FIGS. 5 and 5A for the description of a transvenous endocardial lead 44 representing one embodiment of the invention. In this instance, an elongated electrical conductor 46 extends through a lumen 48 of a flexible body member 50 which may be of any suitable material such as silicon rubber, polyurethane, or the like. The flexible body member 50 extends between a proximal end at the pacemaker and a distal end 52 and has an outer peripheral surface surrounding the electrical conductor 46.

A flexible head member 56 which, as with the flexible body member 50, may be of any suitable material such as silicon rubber, polyurethane, or the like, is recessed as at 58 for integral attachment to the body member 50. An electrically conductive electrode 60 is suitably provided at the distal end of the head member 56 and is electrically connected to the conductor 46. It will be appreciated that the head member 56 and the flexible body member 50 of the transvenous lead 44 may be considered to be of one-piece construction and are illustrated as being of two-piece construction only for ease of manufacture and assembly.

The head member 56 has a continuous groove 62 in and encircling its peripheral surface and lying in a plane generally perpendicular to its longitudinal axis. Unique to the invention is a nonconducting stabilizer 64 which is in the form of a swellable collar embedded in the continuous groove 62 and which extends around the perimeter of the head member adjacent the distal electrode 60. The collar has an outer surface which, in a diminished condition (FIGS. 5 and 5A), is generally flush with the outer peripheral surface 63 and is expandable to a swelled condition (FIGS. 6 and 6A) projecting away from the outer peripheral surface. The collar is composed of a material which is generally inert to body fluids and tissue, which in the dry state remains in a diminished condition but which when exposed to body fluid will absorb the fluid and expand to the swelled condition, and which is pliant yet with sufficient rigidity to engage and be entrapped within fibrous tissue of the heart such as the fine trabeculae 68. The fine trabeculae is a band of fibrous or muscular tissue extending from the inner wall of the heart into the interior of the heart and this tissue prevents dislodgment of the distal electrode from its intended implanted position and the leading surface 66 (FIG. 6) of the collar additionally prevents penetration of the distal electrode into the myocardial tissue 36 of the heart distally beyond the stabilizer 64. The swellable collar may be fabricated or molded using a sodium chloride medical adhesive mixture and the extent of the collar swelling can be controlled by changing the mixture ratio. A typical material suitable for the purpose is manufactured by Dow Chemical Company of Midland, Michigan under the trademark Silicone Medical Adhesive, Grade 891.

When the collar of the stabilizer 64 is in its expanded condition, its outermost surface 70 extends outwardly from the outer peripheral surface 63 of the head member 56 by a distance no greater than approximately one-half of the shortest distance between the longitudinal axis of the head member and the outer peripheral surface 63. This is a preferred dimensional range for minimizing dislodgment of the distal electrode 60 from an intended implanted position and for preventing penetration of the distal electrode into the myocardial tissue of the heart distally beyond the stabilizer 64.

In order to achieve to the optimal extent the effect of minimizing dislodgment of the distal electrode 60 from an intended implanted position while also preventing penetration of the distal electrode into the myocardial tissue of the heart distally beyond said stabilizer, it is desirable to use the above-described construction in combination with known passive fixation devices. Typically, such a passive fixation technique includes the use of nonconductive elongated tines on the head member 56 and extending from the outer peripheral surface 63 at a plurality of spaced locations around the perimeter thereof distant from the distal electrode 60 for cooperating with the myocardial tissue of the heart to hold the head member in position. The tines form a generally acute angle with the outer peripheral surface 63 and are entirely of a pliant material having sufficient rigidity to maintain the angle when the tines are unrestrained, but being sufficiently pliant to prevent penetration of the myocardial tissue of the heart. The pliant material is preferably the same as that of the head member 56, being integral therewith, being generally inert to body fluids. The tines 70 prevent gross dislodgment of the body member 56 relative to the heart 20 while the stabilizer 64 predislodgment dislodgment of said distal electrode 60 from the desired implanted position from or into the myocardial tissue of the heart.

In some instances, it may be desirable to use the stabilizer 64 in combination with an active fixation construction for attaching the endocardial lead to the surface of the heart. In FIGS. 7, 7A, 8, and 8A, such an active fixation construction is illustrated for use with a flexible body member 72 and includes a corkscrew distal end 74 at the terminus of an electrical conductor 76 for penetrating the myocardial tissue of the heart to embed therein the endocardial lead. FIGS. 7 and 7A illustrate the diminished condition of the stabilizer 64 and FIGS. 8 and 8A illustrate its expanded condition.

Figure 9A:
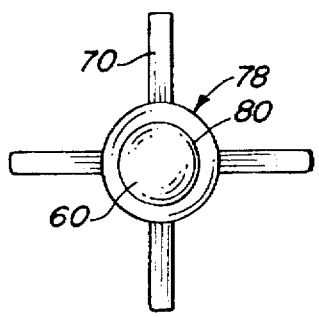
FIGS. 9 and 9A are, respectively, a detail side elevation view, and a front elevation view, similar to FIGS. 6 and 6A, illustrating another embodiment of the invention.
Figure 9:
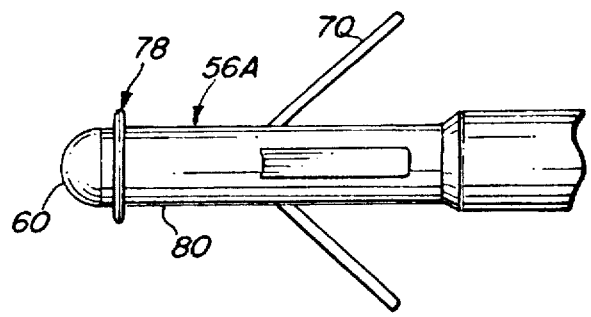

Another embodiment of the invention is illustrated in FIGS. 9 and 9A as stabilizer 78 which includes a continuous annular flange fixed on a modified flexible body member 56A and projects outwardly from the outer peripheral surface 80. As with the stabilizer 64, the annular flange is composed of a material which is generally inert to body fluids and tissue and which is pliant yet with sufficient rigidity to engage and be entrapped within fibrous tissue of the heart.

Figure 10A:
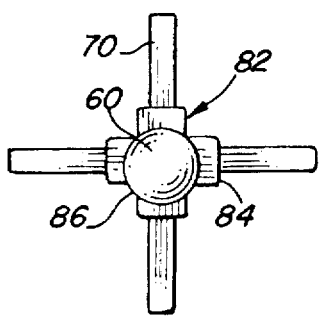
FIGS. 10 and 10A are, respectively, a detail side elevation view, and a front elevation view, similar to FIGS. 6 and 6A, illustrating still another embodiment of the invention.
Figure 10:
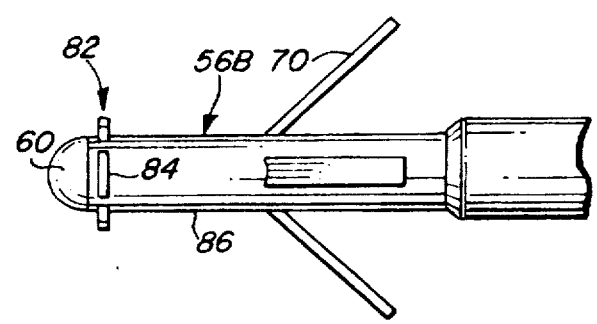

Still another embodiment of the invention is illustrated in FIGS. 10 and 10A as stabilizer 82 which includes a plurality of flange members 84 fixed on the flexible body member 56B and projecting outwardly from the outer peripheral surface 86 thereof at spaced locations around its perimeter. As previously, the flange members are composed of a material which is generally inert to body fluids and tissue and which is pliant yet with sufficient rigidity to engage and be entrapped within fibrous tissue of the heart.

Figure 11A:
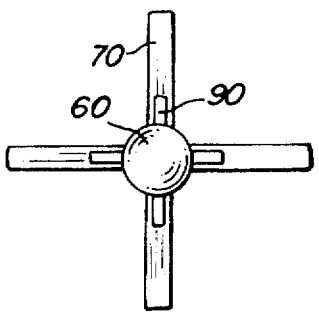
FIGS. 11 and 11A are, respectively, a detail side elevation view, and a front elevation view, similar to FIGS. 6 and 6A, illustrating yet another embodiment of the invention.
Figure 11:
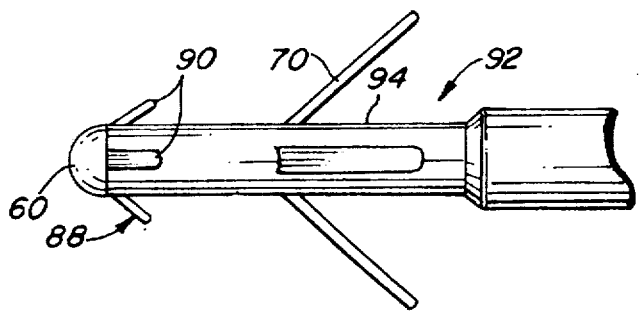

Yet another embodiment of the invention is illustrated in FIGS. 11 and 11A as stabilizer 88 which includes a plurality of nonconductive mini-tines 90 on the flexible body member 92 and extending from the outer peripheral surface 94 at a plurality of spaced locations around the perimeter thereof for cooperating with the myocardial tissue of the heart to hold the flexible body member in position. The mini-tines 90 form a generally acute angle with the outer peripheral surface 94 and are entirely of a material which is pliant yet with sufficient rigidity to engage and be entrapped within fibrous tissue of the heart.

Figure 12A:
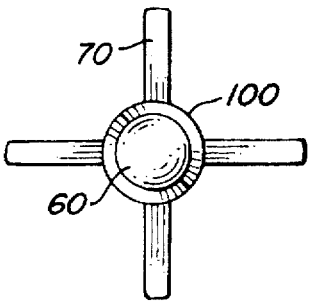
FIGS. 12 and 12A are, respectively, a detail side elevation view, and a front elevation view, similar to FIGS. 6 and 6A, illustrating still a further embodiment of the invention.
Figure 12:
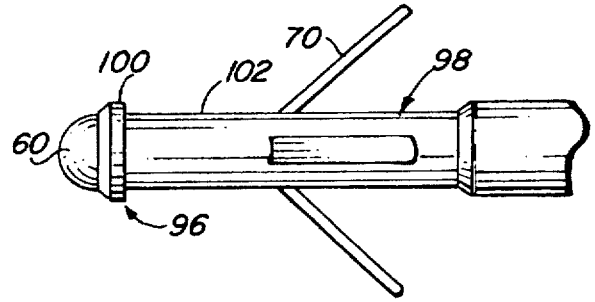

Still a further embodiment of the invention is illustrated in FIGS. 12 and 12A as stabilizer 96 which includes a continuous annular ridge 100 fixed on the flexible body member 98 and projecting outwardly from the outer peripheral surface 102. The annular ridge 100 is composed of the same material as the body member 98 of which it is an integral part, namely, a material which is generally inert to body fluids and tissue and which is pliant yet with sufficient rigidity to engage and be entrapped within fibrous tissue of the heart.

Figure 13A:
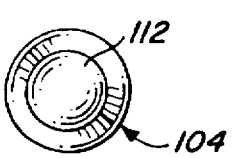
FIGS. 13 and 13A are, respectively, a detail side elevation view, and a front elevation view, similar to FIGS. 12 and 12A, illustrating yet a further embodiment of the invention.
Figure 13:
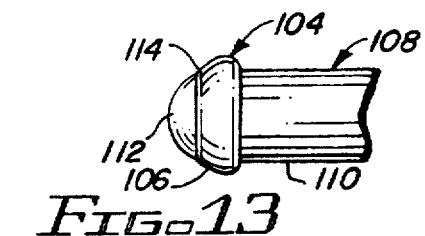

Yet a further embodiment of the invention is illustrated in FIGS. 13 and 13A as stabilizer 104 which includes a continuous annular ridge 106 fixed on the flexible body member 98 and projecting outwardly from the outer peripheral surface 110. The annular ridge 106 is integral with the body member 108, projects away from the outer peripheral surface 110 hereof and is composed of the same material as the body member as in previous embodiments. In this instance, a micro tip electrode 112 is of even smaller size than the electrodes of previous embodiments and a leading edge 114 thereof is continuously smoothly contoured from the surface of the electrode.

In any of the embodiments described, the nominal projected surface area of the distal electrode is in the range of approximately 0.5 to 3.0 mm$^2$.

To recapitulate, a new lead distal end concept may be used for either active (screw-in) or passive (tined, finned) fixation leads intended to minimize distal end dislodgment and myocardium perforation without compromising the small introduction-size lead body and small tip electrode features. In one instance, a swellable elastomer collar is installed right behind the pacing tip electrode. The size of this collar is intended to be small enough to accommodate the size of the recommended lead introducer. The swellable collar may be fabricated or molded using a sodium chloride medical adhesive mixture and the extent of the collar swelling can be controlled by changing the mixture ratio. A few hours after lead implant and being exposed to body fluid, the dry collar will absorb fluid and swell to a size substantially larger than its original size at dry condition. The plump and swelled collar at the tip electrode will reduce the tip pressure, thus minimizing the lead perforation.

In another instance, short, soft and bendable elastomer multi-radial tines or in the form of a single ring is located near the distal electrode.

These features will be easily collapsed or bent into the lead introducer during the lead implantation procedure. Their function is similar to the above-described concept to prevent dislodgment of the distal electrode and to reduce the tip pressure at the distal electrode.

In still another instance, a mini tine or small annular ridge proximate the tip electrode may be employed to anchor the lead into "fine trabeculae" structure of the heart. A major problem is customarily experienced with high impedance pacing leads because of their sensitivity to micromovement due to the small contact area of the tip electrode. This design is effective for reducing this problem especially for small diameter electrodes (that is, those with a surface area of approximately 0.3–2.5 mm$^2$). It may also be desirable to employ the standard tine for its usual purpose in combination with the invention.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A transvenous endocardial lead for electrical stimulation of the heart, the lead having a length, the lead, comprising:

an elongated electrical conductor extending the length of the lead;

a flexible body member extending between proximal and distal ends thereof, said flexible body member having a longitudinal axis and an outer peripheral surface and surrounding the electrical conductor, said flexible body member having a lumen therein for receiving the electrical conductor;

electrically conductive electrode means secured to said distal end of said flexible body member and electrically connected to the electrical conductor for stimulating myocardial tissue of the heart; and nonconducting stabilizing means adjacent said electrode means and extending outwardly from said outer peripheral surface by a distance no greater than approximately one-half of the shortest distance between the longitudinal axis and said outer peripheral surface for minimizing dislodgment of said distal end of said flexible body member from an intended implanted position and for preventing penetration of said distal end of said flexible body member into the myocardial tissue of the heart distally beyond said stabilizing means, wherein said stabilizing means includes a swellable collar fixed on and extending around the perimeter of said outer peripheral surface of said flexible body member adjacent said electrode means, said collar having an outer surface which, in a diminished condition, is generally flush with said outer peripheral surface and is expandable to a swelled condition projecting away from said outer peripheral surface, said collar being composed of a material which is generally inert to body fluids and tissue, which in the dry state remains in a diminished condition but which when exposed to body fluid will absorb the fluid and expand to the swelled condition, and which is pliant yet with sufficient rigidity to engage and be entrapped within fibrous tissue of the heart and prevent further distal travel of said endocardial lead into the myocardial tissue of the heart distally beyond said stabilizing means.

2. A transvenous endocardial lead, as set forth in claim 1:

wherein said flexible body member has a continuous groove in and encircling said peripheral surface and lying in a plane generally perpendicular to said longitudinal axis; and wherein said swellable collar is embedded in the continuous groove and extends around the perimeter of said flexible body member adjacent said electrode means.

3. A transvenous endocardial lead, as set forth in claim 1, including passive fixation means for attaching said endocardial lead to the surface of the myocardial tissue of a heart to be stimulated.

4. A transvenous endocardial lead, as set forth in claim 3, wherein said passive fixation means includes nonconductive tine means on said flexible body member and extending from said outer peripheral surface at a plurality of spaced locations around the perimeter thereof distant from said electrode means for cooperating with the myocardial tissue of the heart to hold said flexible body member in position, said tine means forming a generally acute angle with said outer peripheral surface and being entirely of a pliant material having sufficient rigidity to maintain said angle when said tine means are unrestrained, but sufficiently pliant to prevent penetration of the myocardial tissue of the heart, said pliant material being generally inert to body fluids, said tine means preventing gross dislodgment of said body member relative to the heart, said stabilizing means preventing micro dislodgment of said distal end from the desired implanted position in the myocardial tissue of the heart.

5. A transvenous endocardial lead, as set forth in claim 1, including active fixation means for attaching said endocardial lead to the surface of a heart to be stimulated.

6. A transvenous endocardial lead, as set forth in claim 5, wherein said active fixation means includes a corkscrew distal end on said electrical conductor for penetrating the myocardial tissue of the heart to embed said endocardial lead therein.

7. A transvenous endocardial lead, as set forth in claim 1, wherein the nominal projected surface area of said electrode means is in the range of approximately 0.5 to 3.0 mm$^2$.

* * * * *